US012446990B1

(12) United States Patent
Shields et al.

(10) Patent No.: US 12,446,990 B1
(45) Date of Patent: Oct. 21, 2025

(54) MEDICAL BODY SHIELD

(71) Applicant: The Government of the United States of America, as represented by the Secretary of the Navy, Arlington, VA (US)

(72) Inventors: Garry E. Shields, Ashburn, VA (US); Michael Wade, Ijamsville, MD (US); James G. Mattern, Gainesville, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1154 days.

(21) Appl. No.: 17/358,372

(22) Filed: Jun. 25, 2021

Related U.S. Application Data

(60) Provisional application No. 63/043,875, filed on Jun. 25, 2020.

(51) Int. Cl.
*A61B 90/40* (2016.01)
*A61G 10/00* (2006.01)

(52) U.S. Cl.
CPC ............ *A61B 90/40* (2016.02); *A61G 10/005* (2013.01)

(58) Field of Classification Search
CPC .............................. A61B 90/05; A61G 10/005
See application file for complete search history.

(56) References Cited

U.S. PATENT DOCUMENTS 5,015,864 A * 5/1991 Maleki ...................... G21F 3/02 250/516.1

FOREIGN PATENT DOCUMENTS

| | | | | | |
|---|---|---|---|---|---|
| CN | 1787854 | A | * | 6/2006 | |
| CN | 108318912 | A | * | 7/2018 | |
| CN | 110767341 | A | * | 2/2020 | |
| CN | 118016336 | A | * | 5/2024 | |
| DE | 102020130246 | B3 | * | 5/2022 | |
| KR | 20100016368 | A | * | 2/2010 | |
| TW | M596583 | U | * | 6/2020 | |
| WO | WO-2012116030 | A1 | * | 8/2012 | ............. A47B 83/00 |
| WO | WO-2021247694 | A1 | * | 12/2021 | |

* cited by examiner

*Primary Examiner* — Charles A Marmor, II
*Assistant Examiner* — Marc D. Honrath
(74) *Attorney, Agent, or Firm* — Dawn C. Russell; Jesus J. Hernandez

(57) ABSTRACT

A medical body shield is provided, which includes a center panel formed from a visually-transparent material. The medical body shield protects a user from infectious diseases, while providing the physical access and manual dexterity needed to interact with one or more individuals who are infected (or suspected of being infected). The medical body shields may be used in methods of conducting testing and/or administering treatments.

16 Claims, 4 Drawing Sheets

100

MEDICAL BODY SHIELD

RELATED APPLICATION DATA

This application claims priority under 35 U.S.C. § 119(e) to U.S. Provisional Application No. 63/043,875, filed on Jun. 25, 2020. The entire contents of this provisional application are incorporated herein by reference.

FIELD OF THE INVENTION

Medical body shields are provided, which include a center panel formed from a visually-transparent material. The medical body shield protects a user from infectious diseases, while providing the physical access and manual dexterity needed to interact with one or more individuals who are infected (or suspected of being infected). The medical body shields may be used in methods of conducting testing and/or administering treatments.

BACKGROUND OF THE INVENTION

Medical personnel have traditionally worn personnel protective equipment (PPE), which includes gowns, gloves, respirators, goggles, face shields, and shoe covers, when treating patients who are infected, or suspected to be infected, with contagious diseases.

The global coronavirus pandemic resulted in nationwide shortages of PPE. These shortages forced health care workers to assume unacceptable levels of risk while caring for patients suffering from the coronavirus disease 2019 (COVID-19) caused by infection with the SARS-CoV-2 virus. These risks included reusing PPE, working with improvised PPE of unknown effectiveness, or working with no PPE at all.

Accordingly, a need exists in the art for alternatives to traditional disposable items of PPE that provide protection to people at high risk of exposure to infectious diseases.

SUMMARY OF THE INVENTION

The apparatus and methods of the invention address a critical need to develop alternative protective barriers, which may be used, for example, by medical professionals and other workers during interactions with people who may be infected with infectious diseases. The invention is designed to improve the safety of workers while providing treatment and testing services to patients suffering from infectious diseases, such as COVID-19. The invention may also help to minimize the amount of PPE that workers must wear, enabling PPE resources to be conserved for use in higher-risk settings and procedures, such as administering treatments requiring close patient contact.

In a first aspect of the invention, a medical body shield is provided, which includes a central panel having circular arm slots. The medical body shield includes a rectangular frame having horizontal support members, vertical support members, central panel height adjustment rails provided on the vertical support members, and central panel height adjustment locks. The central panel is slidably mounted in the central panel height adjustment rails, and maintained in a fixed position relative to the horizontal support members by the central panel height adjustment locks. In some aspects of the invention, the central panel includes at least a portion formed from a visually-transparent material.

In another aspect of the invention, methods are provided for protecting a health care worker while testing patients for an infectious disease. The methods include providing a medical body shield having a central panel comprising circular arm slots; a rectangular frame including horizontal support members, vertical support members, central panel height adjustment rails provided on the vertical support members, and central panel height adjustment locks. The central panel is slidably mounted in the central panel height adjustment rails, and is maintained in a fixed position relative to the horizontal support members by the central panel height adjustment locks. The health care worker is positioned behind the central panel of the medical body shield. The position of the central panel is adjusted along a vertical axis, relative to the horizontal support members, to protect the health care worker from direct contact with infectious disease-causing microorganisms while testing patients suspected of being infected with an infectious disease.

In a further aspect of the invention, methods are provided for reducing health care worker risk when treating a patient suffering from an infectious disease. The methods include providing a medical body shield having a central panel comprising circular arm slots; a rectangular frame including horizontal support members, vertical support members, central panel height adjustment rails provided on the vertical support members, and central panel height adjustment locks. The central panel is slidably mounted in the central panel height adjustment rails, and maintained in a fixed position relative to the horizontal support members by the central panel height adjustment locks. The patient to be treated is positioned in front of the central panel of the medical body shield. The health care worker is positioned behind the central panel of the medical body shield to treat the patient. The vertical position of the central panel is adjusted to facilitate treatment of the patient by the health care worker, while preventing the health care worker from coming into direct contact with infectious microorganisms during interactions with the patient suffering from an infectious disease.

Other features and advantages of the present invention will become apparent to those skilled in the art upon examination of the following or upon learning by practice of the invention.

BRIEF DESCRIPTION OF THE DRAWINGS

In FIG. 3A, the side panels are oriented at a 90° angle with respect to the central panel. In FIG. 3B, the side panels are oriented at a 45° angle with respect to the central panel.

DETAILED DESCRIPTION OF THE INVENTION

Figure 1B:
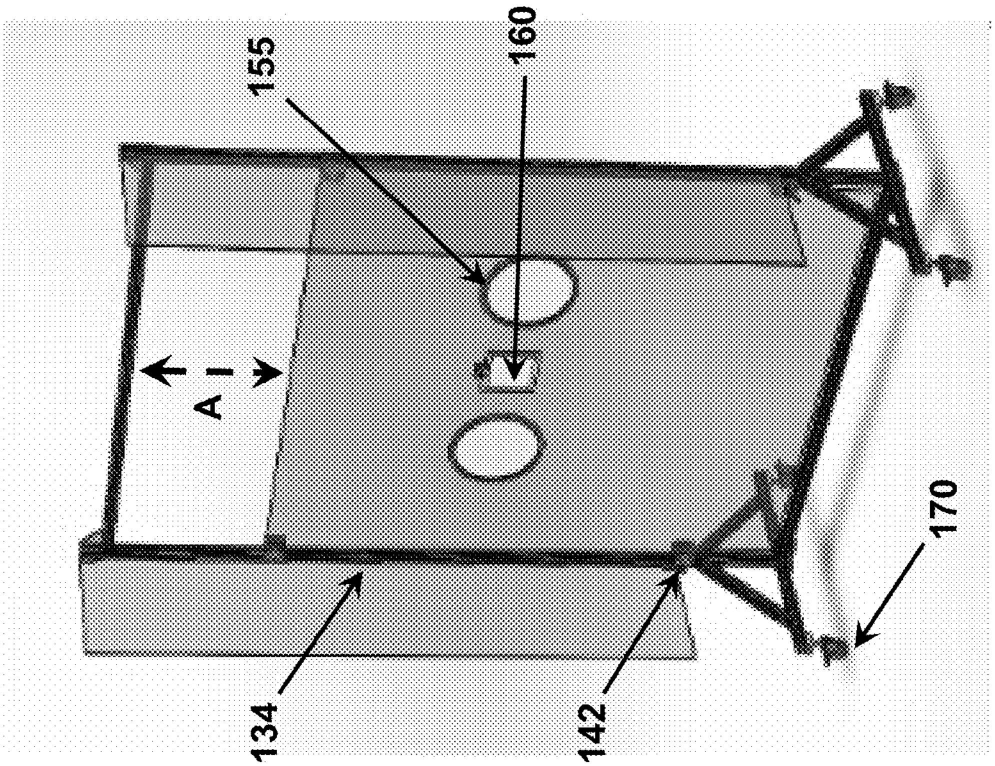
FIGS. 1A and 1B show a medical body shield in accordance with the invention, with an adjustable central panel depicted in its upper (FIG. 1A) and lower (FIG. 1B) positions. The side panels extend toward the medical care provider when the medical body shield is in use.

The inventions described herein provide medical body shields that include a center panel formed at least in part from a visually-transparent material. The medical body shield protects a user from infectious diseases, while providing the physical access and manual dexterity needed to interact with one or more individuals who are infected (or suspected of being infected). The medical body shields may be used in methods of conducting testing and/or administering treatments.

The medical body shields of the invention beneficially protect medical personnel from exposure to patients suspected of carrying infectious diseases, while reducing or eliminating the need for other types of personal protective equipment (PPE) such as masks, gloves, and gowns. This is particularly helpful when widespread exposure to an infectious disease is suspected within a population, and it is impractical to remove and replace PPE between each patient encounter.

The medical body shields of the invention include a central panel mounted on a frame that provides support and stability to the central panel, and may be designed with wheels, casters, or other means of conveying the medical body shield. In some aspects of the invention, the central panel includes at least a portion formed from a visually-transparent material, and in other aspects, the entire central panel is formed using a visually-transparent material. The medical body shields may also incorporate features including, but not limited to, circular arm slots fitted with glove attachment sealing rings, one or more ports for speaking and listening, fixed or adjustable side protection panels, diagnostic equipment holders (for pulse oximeters, stethoscopes, etc.), and testing equipment holders (for swabs, envelopes, test tubes, etc.). Preferably, any diagnostic and/or testing equipment holders are positioned on the patient-facing side of the central panel so as to be within the reach of the health care worker when his/her arms are extended through the circular arm slots towards a patient.

The medical body shield frame includes vertical and horizontal support members in a rectangular configuration. The frame may include central panel height adjustment rails mounted on or integrated into one or both vertical support members, and a central panel height adjustment locking mechanism to fix the vertical position of the central panel relative to the central panel height adjustment rail. The range of height adjustment can be dependent on the height of the central panel, the height of the health care worker, the position of the health care worker (i.e., sitting, standing), and the position of the patient (i.e., prone, supine, standing, sitting in chair, sitting in car). In some aspects of the invention, the central panel may be adjusted upward by up to about 16", or downward by up to about 16", for a total height adjustment range of about 32". In use, the locking mechanism is released and the central panel is moved upward or downward within the height adjustment rails until a suitable position is attained. At this point, the locking mechanism is re-engaged to fix the vertical position of the central panel with respect to the medical body shield frame. Preferably, the position is adjusted prior to initiating patient encounters, to minimize accidental contact with areas of the medical body shield that may have been exposed to patients being tested or treated, though adjustment during patient encounters is also envisioned within the scope of the invention.

The frame may also be configured to support side panels, which further limit the degree of exposure to infectious agents that may be conveyed by respiration, coughing, sneezing, or vomiting of the patient. Preferably, the side panels have a width sufficient to extend behind the health care worker while the medical body shield is in use, but the width of the side panel may range from about 12" to about 36", preferably about 18" to about 24". The side panels may be held in position by mounting them to the frame at a fixed angle, for example, from about a 45° angle to about a 135° angle with respect to the center panel. In other aspects of the invention, the side panels may be affixed to the frame in a manner that permits the angle with respect to the center panel to be adjusted, from about 45° angle (extending inward toward the medical care worker) to about 180° angle (extending out parallel to the central panel).

These and additional features of the medical body shields of the invention are now described by reference to the drawings.

Figure 1A:
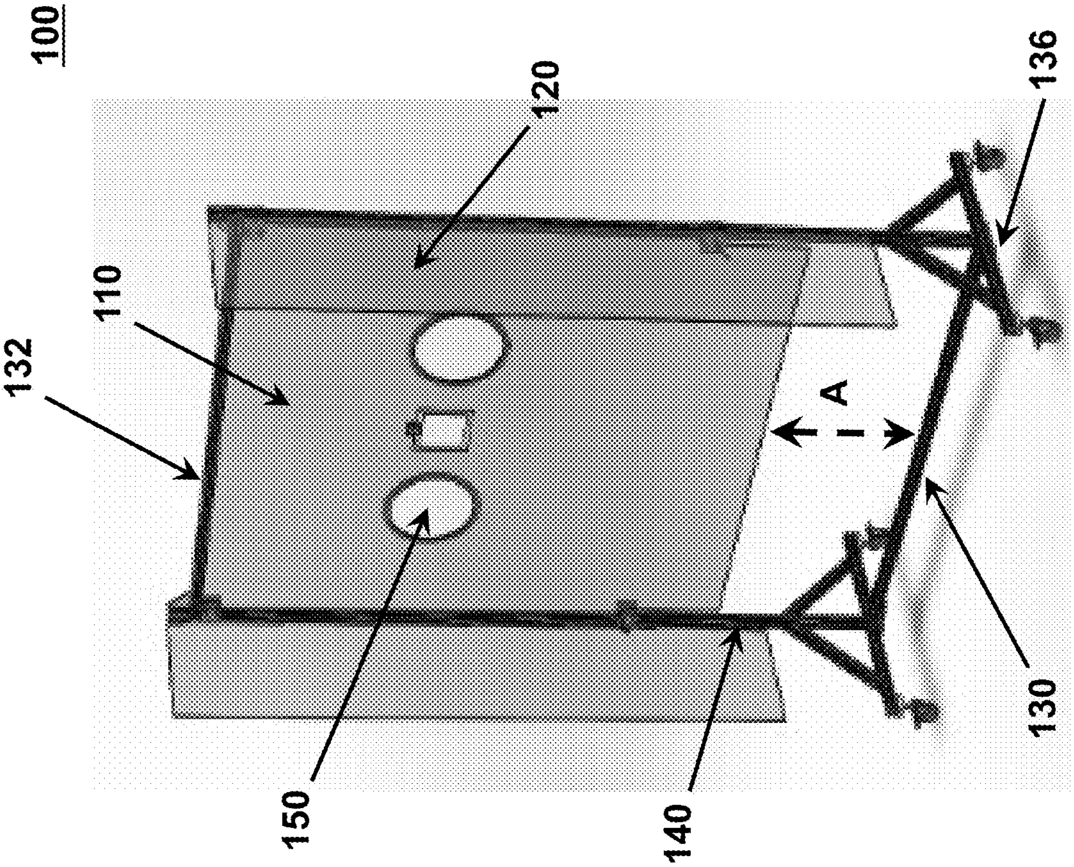

As shown in FIGS. 1A and 1B, the medical body shield 100 includes a central panel 110 and two side panels 120. The panels 110 and 120 may be made in whole or in part from one or more visually-transparent materials, permitting the health care worker to carefully observe and interact with the potentially-infected patient. In some aspects of the invention, the transparent material is a plastic material, such as optically-transparent polycarbonate or acrylic, or silica-based glass. The transparent material allows the health care provider to observe the patient during their interaction, and provides a more personal experience for the patient. For portions of the medical body shield 100 that are not used to view a patient during an encounter, a non-transparent material may be used, such as stainless steel, aluminum, or plastic.

In some aspects of the invention, the visually-transparent portions of the medical body shield may have a coating applied, for example, to reduce glare, or to block UV radiation. In other aspects of the invention, coatings may be applied to all surfaces of the medical body shield, for example, to provide antimicrobial properties.

Both the central panel 110 and side panels 120 mount onto a support frame 130. The support frame 130 is preferably a rectangular frame that includes two vertical and two horizontal support members, all made from a strong, lightweight material, such as extruded aluminum. Alternative frame materials may include steel or other metals. The frame may include a base 136 for stability, and the base of the frame may be mounted on wheels or casters 170 that can be locked in position once the medical body shield 100 is moved to the desired location.

In aspects of the invention where the positions of the panels 110, 120 are fixed, the panels may be directly attached to horizontal 132 and vertical 134 support frame members. Although permanent attachments such as bolts and screws may be used (not shown) where ability to adjust the panel heights is not required, in some aspects of the invention the attachment points may be releasable (such as clips, clamps, hinges, or slots in the panels that attach to pins provided on the frame). The type of attachment may facilitate adjustment of the angle of the side panels 120 with respect to the central panel 110, or removal of the panels for cleaning. The attachment may also permit side panels 120 to be fixed into position at a specific angle relative to the healthcare worker-facing side of the central panel 110 (e.g., 90°, 120°).

In presently-preferred aspects of the invention, the center panel 110 is slidably mounted on the support frame 130. The height of the central panel 110 can be adjusted up (FIG. 1A) or down (FIG. 1B) relative to the horizontal support frame members 132, as shown by axis A. The central panel 110 is configured to be adjusted to accommodate the height of the user being protected, or to adapt to the particular use conditions. Central panel height adjustment rails 140 are preferably installed on both vertical support frame members 134, allows the central panel 110 to slide up and down to adjust its height relative to the surface on which the medical body shield 100 is resting (which may include, without limitation the ground, a floor, or a raised platform). This feature provides the medical worker with the greatest possible access to the patient while providing maximum personal safety. The central panel 110 may be fixed in place, for example, by employing central panel height adjustment locking mechanisms 142.

Figure 2A:
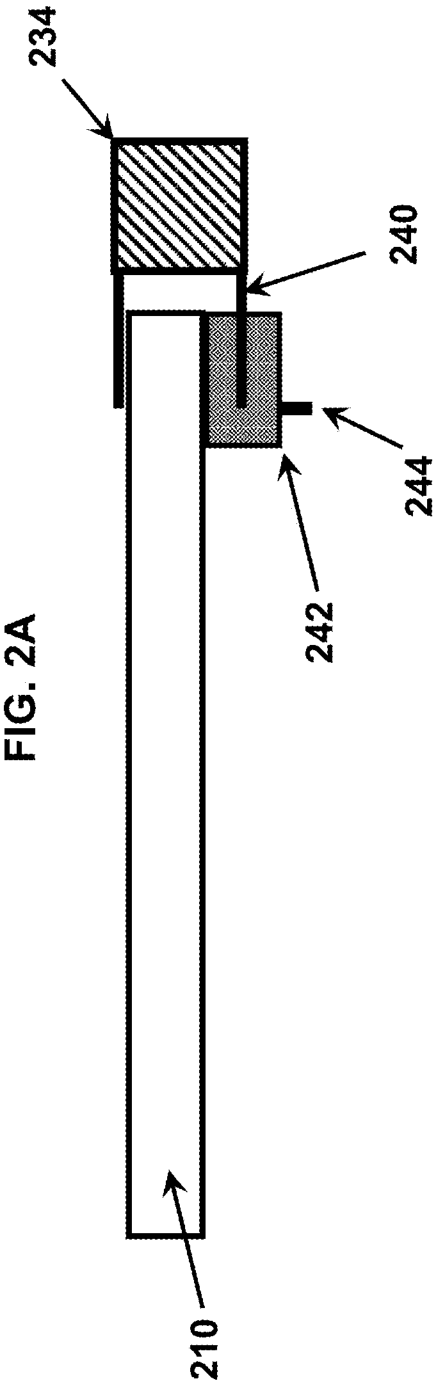
FIGS. 2A and 2B show a top view of the adjustable central panel provided within height adjustment rails provided on vertical members of the medical body shield frame. A clamp for fixing the position of the panel is depicted in FIG. 2A. A pin for fixing the position of the panel is depicted in FIG. 2B.
Figure 2B:
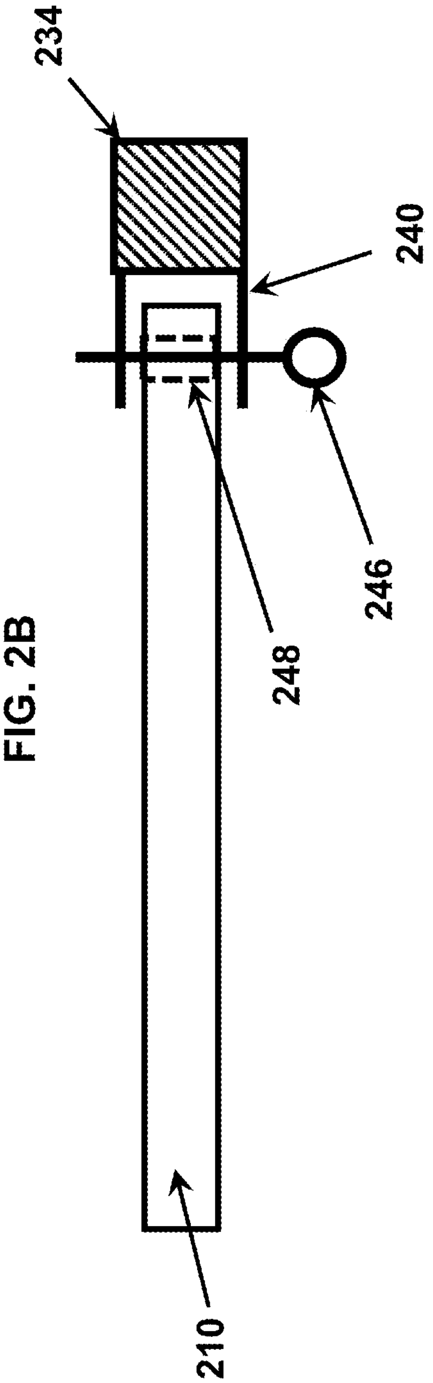

Examples of central panel adjustment mechanisms suited for use with the medical body shield of the invention are shown in FIGS. 2A and 2B, though the invention is not to be considered limited to any specific type of locking mechanism. Preferably, the locking mechanism is provided on the side of the medical body shield facing the worker, to prevent a patient from moving the panel during a treatment or testing encounter. Any locking mechanism suitable for holding the slidable central panel 210 securely in place during patient treatment encounters is within the scope of the invention. As shown in FIG. 2A, one example of a locking mechanism is clamp 242. The clamp 242 may be engaged to secure the central panel 210 within height adjustment rail 240, which is mounted on vertical support frame member 234. Clamp 242 may be actuated by the health care worker using a thumb latch, screw, or other mechanism 244 for applying pressure to secure the central panel 210 within the height adjustment rail 240. In FIG. 2B, a pin and slot is shown as another example of a locking mechanism for use in the medical body shield of the invention. In this configuration, pin 246 slides through locking holes provided at regular intervals over the length of height adjustment rail 240 and through (optionally reinforced) holes 248 through central panel 210 that are configured to provide a range of height adjustment.

The height adjustable medical body shield design as shown in FIGS. 1A and 1B supports medical workers of varying heights, and accommodates workers performing a variety of tasks, such as outdoor drive-through or walk-up COVID-19 testing, which may be conducted with the patient standing or sitting. Those skilled in the art will appreciate that larger or smaller height adjustment ranges may be provided by lengthening or shortening the height adjustment rails 140, and raising or lowering the positions of locking points 142 on the height adjustment rails 140.

The central panel 110 preferably includes two circular arm slots 150 that a medical worker uses by donning gloves and inserting their arms through the circular arm slots 150. This enables the medical worker to reach the patient on the patient-facing side of the central panel 110. Each circular arm slot 150 may be provided with a glove attachment sealing ring 155 installed around the inside rim. Each glove attachment sealing ring 155 may include a threaded insert to create an airtight seal between the shield and the glove. This shield design feature beneficially permits the use of arm-length gloves. The open end of a glove pulls over an elevated lip on the inside surface of the sealing ring. The threaded insert screws into the sealing ring receiver from inside the shield and seals the glove into place. If equipped with gloves secured by the glove attachment sealing rings 155, the medical body shield of the invention provides a complete barrier against contact with infectious agents for the health care worker using it.

Conducting patient care or testing procedures using the medical body shield of the invention reduces the risk of exposure to infectious agents as compared to conducting the patient care or testing procedures without the medical body shield, give the same use of PPE. When the medical body shield is used in an environment with adequate circulation (i.e., outdoors, or within a building having adequate airflow, filtration, and optionally supplemental irradiation), the medical body shield further reduces the risk of exposure to infectious agents, and may allow the health care worker to reduce the amount of PPE used during patient encounters.

One or more optional ports 160 for speaking and listening to the patient may be provided in the central panel 110, which may optionally include a replaceable high-efficiency particulate arrestance (HEPA) filter to trap any potentially-infectious particles. As shown in FIGS. 1A and 1B, the voice port 160 is located between the circular arm slots 150, but alternative placements are also envisioned in accordance with the invention. The port 160 allows the medical worker to communicate with the patient without compromising the integrity of the shield.

The medical body shield of the invention is preferably configured in a manner that facilitates its movement. The base 136 of frame 130 may have wheels, casters, or other means for facilitating its movement within a facility. For example, providing 360° rolling casters 170 on the base 136 of the support frame 130 allow a single person to easily roll, maneuver and position the medical body shield 100.

Figure 3A:
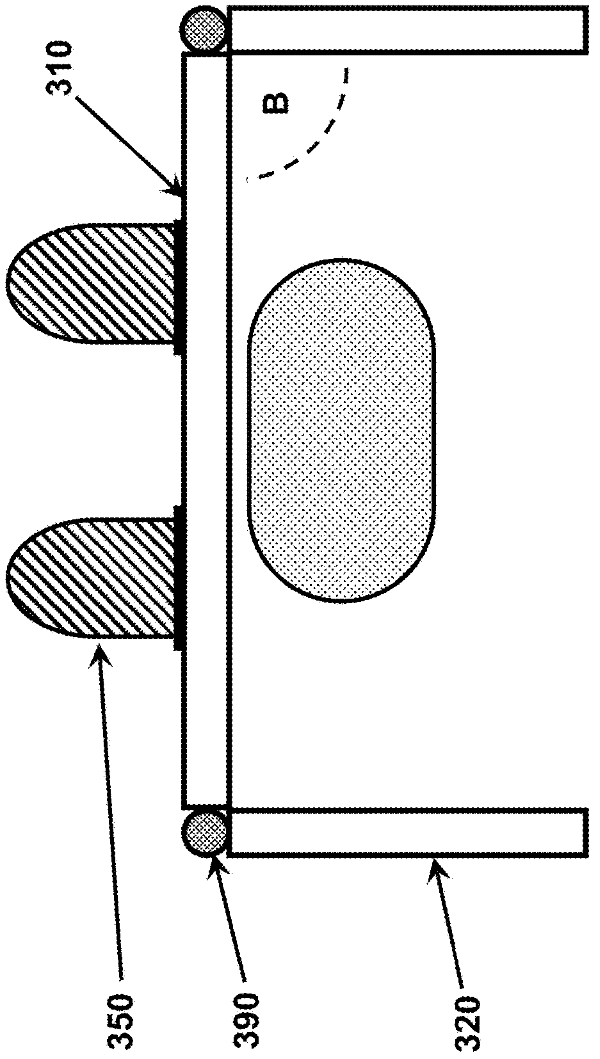
FIGS. 3A and 3B show a top view of the medical body shield, depicting a central panel and two side panels, where the angle of the side panels is adjustable relative to the central panel.
Figure 3B:
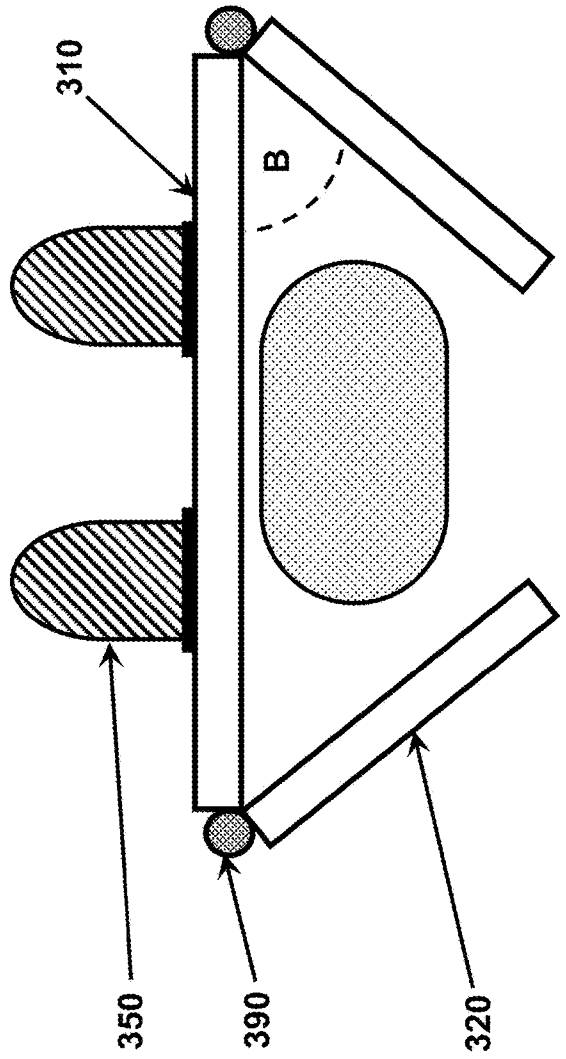

As shown in FIGS. 3A and 3B, the side panels 320 may be oriented at an adjustable angle B with respect to central panel 310. In some aspects of the invention, the angle B can be independently adjusted during use, for example, by affixing the side panels 320 to the support frame (not shown) using hinges 390, or other pivoting or articulating joint between the central panel 310 and side panels 320, or between frame members supporting the panels. The side panels 320 are preferably oriented to provide additional protection to the healthcare worker (depicted using the oval) when interacting with a patient (not shown) on the opposite side of central panel 310 who may be infected with an infectious disease. Gloves 350 are depicted, and when in use, the gloves 350 permit the health care worker to conduct testing protocols or administer medical procedures to the patient without directly contacting the patient.

Figure 4:
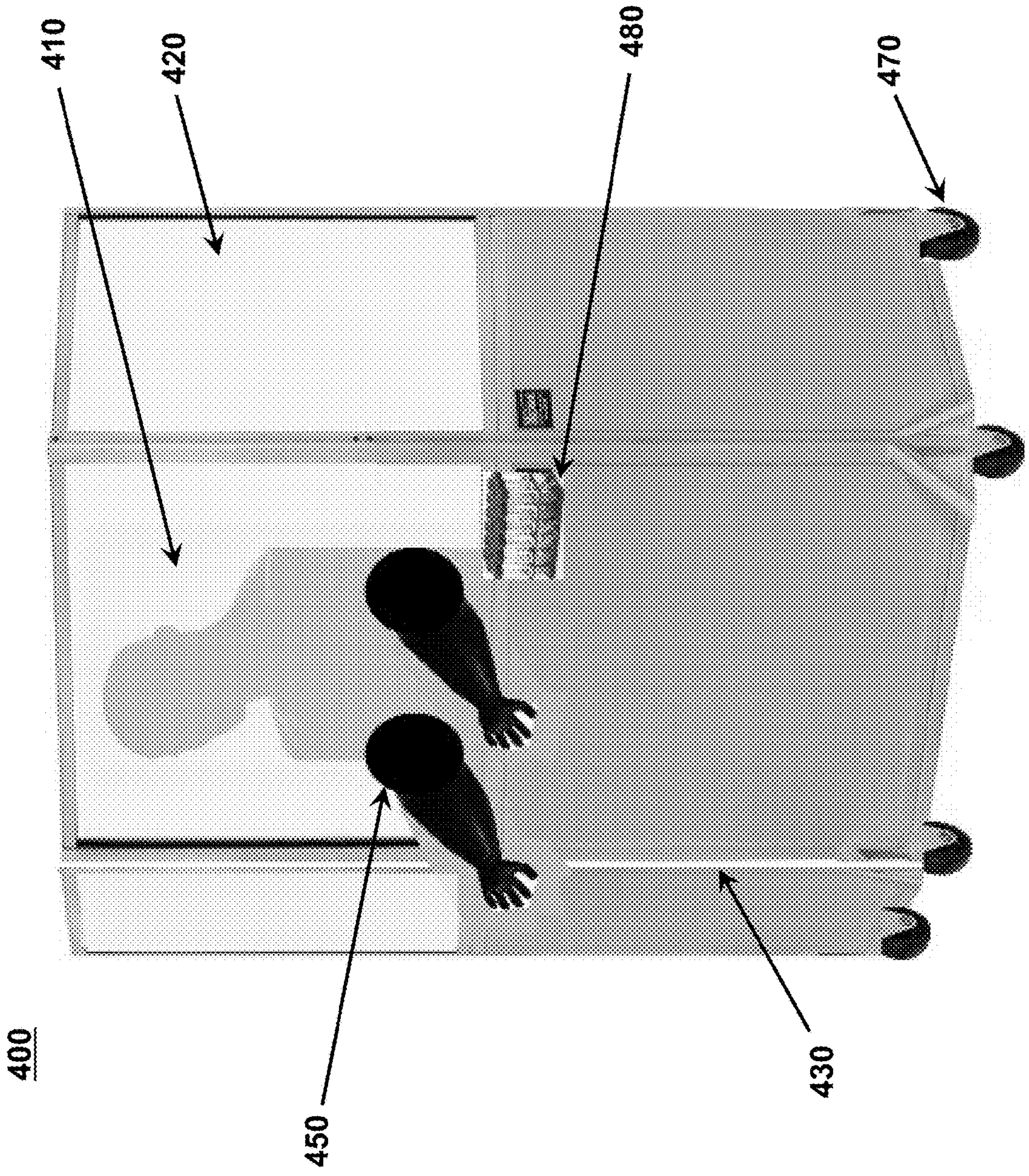
FIG. 4 shows an alternative configuration for a medical body shield in accordance with the invention, which incorporates fixed panels, and a sample holding apparatus affixed to a patient-facing panel.

An alternative configuration for the medical body shield of the invention is depicted in FIG. 4. The medical body shield 400 is formed from panels 410, 420 that incorporate sections of visually-transparent material, with the remainder of the panel formed of a durable material that is readily sanitized and resists degradation by disinfectant chemicals (for example, steel, aluminum, plastic). In this configuration, the height of central panel 410 is not adjustable. The panels 410, 420 are each supported by rectangular frames 430, which may optionally be mounted on wheels 470, such as 360° rolling casters. In some aspects of the invention, the frames 430 may form an integral part of the panels 410, 420. The angle of the panels 420 with respect to the central panel 410 may be adjusted, for example, by providing the sides of the frame on hinges. As an alternative, the angle of the side panels 420 may be fixed at set angle with respect to central panel 410. The fixed angle may vary from about 90° to about 135°.

A medical care provider is depicted behind the medical body shield, and arm-length gloves 450 are attached to the medical body shield 400 using glove attachment sealing rings (not shown). The gloves 450 extend through the medical body shield 400. One or more test sample or supply holders 480 may be provided on the patient-facing side of the medical body shield 400. By providing sample or supply holders 480 on the patient-facing surface of the medical body shield 400, a testing or treatment procedure can be conducted while maintaining a physical barrier between the medical provider behind the medical body shield and the potentially-infectious patient and/or samples. The sample or supply holder may be a means for containing test tubes, such as a test tube rack, or a means for containing testing or treatment supplies. The particular means may vary depending on the type of test or treatment being conducted by the user of the medical body shield 400. Examples include, but are not limited to, boxes, stands, dispensers, pockets, and clamps.

The design of the medical body shield of the invention is easily adapted to accommodate use while conducting different types of testing and treatments, and under varying conditions. For example, when used in drive-up testing centers, the height adjustment of the center panel may facilitate testing individuals arriving in different types of vehicles having different heights (i.e., compact car vs. large truck). When used in patient treatment interactions, the adjustments may support administering care to patients regardless of whether they are lying down, sitting, or standing.

The medical body shields of the invention may be used in methods for protecting a health care worker while testing patients for an infectious disease. The methods include providing a medical body shield having a central panel comprising circular arm slots; a rectangular frame including horizontal support members, vertical support members, central panel height adjustment rails provided on the vertical support members, and central panel height adjustment locks. The central panel is slidably mounted in the central panel height adjustment rails, and is maintained in a fixed position relative to the horizontal support members by the central panel height adjustment locks. The health care worker is positioned behind the central panel of the medical body shield. The position of the central panel is adjusted along a vertical axis, relative to the horizontal support members, to protect the health care worker from direct contact with infectious disease-causing microorganisms while testing patients suspected of being infected with an infectious disease.

The medical body shields of the invention may also be used in methods for reducing health care worker risk when treating a patient suffering from an infectious disease. The methods include providing a medical body shield having a central panel comprising circular arm slots; a rectangular frame including horizontal support members, vertical support members, central panel height adjustment rails provided on the vertical support members, and central panel height adjustment locks. The central panel is slidably mounted in the central panel height adjustment rails, and maintained in a fixed position relative to the horizontal support members by the central panel height adjustment locks. The patient to be treated is positioned in front of the central panel of the medical body shield. The health care worker is positioned behind the central panel of the medical body shield to treat the patient. The vertical position of the central panel is adjusted to facilitate treatment of the patient by the health care worker, while preventing the health care worker from coming into direct contact with infectious microorganisms during interactions with the patient suffering from an infectious disease.

The infectious disease that is to be prevented from being transmitted from the patient to the health care worker is not particularly limited. Reducing the risk of exposure to infectious diseases selected from the group consisting of influenza, COVID-19, Ebola, diphtheria, measles, rubella, mumps, pertussis, and norovirus are all envisioned within the scope of the invention. Preventing exposure to other disease-causing agents is also within the scope of the invention, including those not yet discovered.

In these methods, the medical body shields of the invention are used to provide a physical barrier between the medical care provider and the individual being tested or treated throughout the testing or treatment procedure.

The apparatus of the invention and methods of using the apparatus to protect health care workers and treat patients address a critical need to develop alternative protective barriers, which may be used, for example, by medical professionals to keep themselves safe while treating patients who are potentially infected with infectious diseases, such as COVID-19. The invention may also beneficially help to minimize the amount of PPE that medical workers must wear during patient encounters, enabling PPE resources to be conserved for use in higher-risk settings, such as administering treatments requiring close patient contact.

The medical body shields and methods of the invention provide the following benefits:

- Minimizes the amount of Personal Protective Equipment (PPE) worn by medical personnel.
- Low cost and made out of readily-available materials.
- Reusable and easy to sanitize.
- Reduces medical worker exertion and fatigue.
- Lightweight, portable and highly maneuverable.
- Functional in both indoor and outdoor treatment settings.

It will, of course, be appreciated that the above description has been given by way of example only and that modifications in detail may be made within the scope of the present invention.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A medical body shield, comprising:

a central panel comprising circular arm slots;

a rectangular frame comprising:

horizontal support members, vertical support members, central panel height adjustment rails provided on the vertical support members, and central panel height adjustment locks, wherein the central panel is slidably mounted in the central panel height adjustment rails, a position of the central panel being adjustable along a vertical axis, relative to the horizontal support members, wherein at least one open adjustable gap exists between an end of the central panel and at least one of the horizontal support members, wherein the at least one open adjustable gap comprises a total area, such that the total area of the at least one open adjustable gap remains consistent at any position of the central panel, and wherein the central panel is configured to be maintained in a fixed position relative to the horizontal support members by the central panel height adjustment locks.

2. The medical body shield of claim 1, wherein the central panel comprises at least one holding device mounted on the central panel, the at least one holding device configured to contain at least one of testing and treatment supplies.

3. The medical body shield of claim 2, wherein the at least one holding device is at least one of, or a combination of, a box, a stand, a dispenser, a pocket, and a clamp.

4. The medical body shield of claim 1, wherein the central panel comprises a communication port comprising a filter.

5. The medical body shield of claim 1, wherein the circular arm slots comprising glove attachment sealing rings.

6. The medical body shield of claim 1, wherein at least a portion of the central panel is formed from a visually-transparent material.

7. The medical body shield of claim 6, wherein the visually-transparent material is one of a polycarbonate, an acrylic, a plastic material, and a silica-based glass.

8. The medical body shield of claim 6, wherein the visually-transparent material has a coating, the coating being at least one of a glare-reduction coating, a UV-radiation blocking coating, and an antimicrobial coating.

9. The medical body shield of claim 6, wherein at least a portion of the central panel is made from a non-transparent material, the non-transparent material comprising at least one of stainless steel, aluminum, and plastic.

10. The medical body shield of claim 1, wherein the frame comprises wheels.

11. The medical body shield of claim 1, wherein the central panel is configured to be slidably mounted to be flush with a bottom horizontal support member of the rectangular frame, and wherein the central panel configured to be slidably mounted to be flush with a top horizontal support member, of the rectangular frame.

12. The medical body shield of claim 1, further comprising:

at least two side panels connected to the vertical support members.

13. The medical body shield of claim 12, further comprising:

hinges connecting the at least two side panels to the vertical support members, wherein the at least two side panels are configured to rotate about the hinges and be positioned at an adjustable angle relative to the central panel.

14. The medical body shield of claim 1, wherein the rectangular frame is made of at least one of extruded aluminum and steel.

15. The medical body shield of claim 1, wherein the central panel height adjustment locks are one of a clamp device and a pin device.

16. The medical body shield of claim 15, wherein the clamp device comprises one of a thumb latch and a screw.

* * * * *